United States Patent

Ohki et al.

[11] Patent Number: 5,580,727
[45] Date of Patent: Dec. 3, 1996

[54] AML1-MTG8 FUSION PROTEIN RESULTING FROM T(8;21) TRANSLOCATION IN ACUTE MYELOID LEUKEMIA

[75] Inventors: Misao Ohki, Kokubunji; Kimiko Kikuchi, Tokyo; Hiroyuki Miyoshi, Ageo; Tomoko Kozu, Kitamoto, all of Japan

[73] Assignee: SRL, Inc., Tokyo, Japan

[21] Appl. No.: 244,189

[22] Filed: Aug. 15, 1994

[30] Foreign Application Priority Data

Sep. 29, 1992 [JP] Japan ................................ 4-285520

[51] Int. Cl.⁶ .......................... C12Q 1/68; C12P 19/34; C07H 21/02; C07H 21/04
[52] U.S. Cl. .......................... 435/6; 435/91.2; 536/22.1; 536/23.1; 536/24.3; 536/24.31; 536/24.32; 536/24.33
[58] Field of Search .................... 435/6, 91.2; 536/22.1, 536/23.1, 24.3, 24.31, 24.32, 24.33

[56] References Cited

U.S. PATENT DOCUMENTS 4,683,202  7/1987  Mullis .................................... 435/91

OTHER PUBLICATIONS

Erickson et al, (Oct. 1992), "Identification of breakpoints in t(8;21) acute myelogenous leukemia and isolation of a fusion transcript, AML1/ETO, with similiarity to Drosophila segmentation gene, runt", Blood 80(7):1825–1831.

Miyoshi et al, (1991), "T(8;21) breakpoints on chromosome 21 in acute myeloid leukemia are clustered within a limited region of a single gene, AML1"proc. Natl. Acad. Sci. 88:10431–10434.

Mifflin et al, (1989) "Use and applications of nucleic acid probes in the clinical laboratory"Clin. Chem. 35(9):1819–1825.

Kozu et al, (Aug. 1993), "Junctions of the AML1/MTG8(ETO) fusion are constant in t(8;21) acute myeloid leukemia detected by reverse transcription polymerase chain reaction", Blood 82(4):1270–1276.

Berger et al, (1982), "Cytologic characterization and significance of normal karyotypes in t(8;21) acute myeloblaslic leukemia", Blood 59(1):171–178.

Kozu et al, (1993), "Identification of AML1–MTG8 fusion transcripts generated by the chromosomal translocation t(8;21) in human acute myeloid leukemia", J. Cell. Biochem. Suppl. 17A:215.

Maseki et al, (Mar. 1993), "The 8;21 chromosomes translocation in acute myeloid leukemia is always detectable by molecular analysis using AML1", Blood 81 (6):1573–1579.

Miyoshi et al, (Jul. 1993), "The t(8;21) translocation in acute myeloid leukemia results in production of an AML1–MTG8 fusion transcript", EMBO J. 12(7):2715–2721.

Shimizu et al, (Dec. 1992), "Consistent disruption of the AML1 gene ocurs within a single intron in the t(8;21) chromosomal translocation", Cancer Res. 52:6945–6948.

Primary Examiner—Stephanie W. Zitomer
Assistant Examiner—Jeffrey Fredman
Attorney, Agent, or Firm—Birch, Stewart, Kolasch & Birch, LLP

[57] ABSTRACT

Means for diagnosing t(8;21) translocation type acute myeloid leukemia with high sensitivity by a simple operation are disclosed. The present invention provided AML1-MTG8 fused DNA having the nucleotide sequence shown in SEQ ID No. 1 and DNA fragments thereof containing the fused site. The present invention provided AML1-MTG8 fused polypeptide having the amino acid sequence shown in SEQ ID No. 2, and fragments thereof containing the fused site. The present invention provided AML1-MTG8 fused mRNA having the same nucleotide sequence as shown in SEQ ID No. 1 except that thymine is replaced with uracil, and fragments thereof. The present invention provided a probe which is said DNA fragment that is labelled. The present invention provided a method for detecting said fused DNA by using said probe. The present invention provided a method for detecting AML1-MTG8 fused mRNA or a fragment thereof in a sample, comprising the steps of amplifying said fused DNA or a fragment thereof by a nucleic acid-amplifying method and detecting the amplified DNA fragment.

12 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4287 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 1579..3834

( x i ) SEQUENCE DESCRIPTION: SEQ ID NO:1:

```
CATAGAGCCA  GCGGGCGCGG  GCGGGACGGG  CGCCCCGCGG  CCGGACCCAG  CCAGGGCACC      60

ACGCTGCCCG  GCCCTGCGCC  GCCAGGCACT  TCTTTCCGGG  GCTCCTAGGG  ACGCCAGAAG     120

GAAGTCAACC  TCTGCTGCTT  CTCCTTGGCC  TGCGTTGGAC  CTTCCTTTTT  TTGTTGTTTT     180

TTTTTGTTTT  TCCCCTTTCT  TCCTTTTGAA  TTAACTGGCT  TCTTGGCTGG  ATGTTTTCAA     240

CTTCTTTCCT  GGCTGCGAAC  TTTTCCCCAA  TTGTTTTCCT  TTTACAACAG  GGGGAGAAAG     300

TGCTCTGTGG  TCCGAGGCGA  GCCGTGAAGT  TGCGTGTGCG  TGGCAGTGTG  CGTGGCAGGA     360

TGTGCGTGCG  TGTGTAACCC  GAGCCGCCCG  ATCTGTTTCG  ATCTGCGCCG  CGGAGCCCTC     420
```

```
CCTCAAGGCC CGCTCCACCT GCTGCGGTTA CGCGGCGCTC GTGGGTGTTC GTGCCTCGGA      480
GCAGCTAACC GGCGGGTGCT GGGCGACGGT GGAGGAGTAT CGTCTCGCTG CTGCCCGAGT      540
CAGGGCTGAG TCACCCAGCT GATGTAGACA GTGGCTGCCT TCCGAAGAGT GCGTGTTTGC      600
ATGTGTGTGA CTCTGCGGCT GCTCAACTCC CAACAAACCA GAGGACCAGC CACAAACTTA      660
ACCAACATCC CCAAACCCGA GTTCACAGAT GTGGGAGAGC TGTAGAACCC TGAGTGTCAT      720
CGACTGGGCC TTCTTATGAT TGTTGTTTTA AGATTAGCTG AAGATCTCTG AAACGCTGAA      780
TTTTCTGCAC TGAGCGTTTT GACAGAATTC ATTGAGAGAA CAGAGAACAT GACAAGTACT      840
TCTAGCTCAG CACTGCTCCA ACTACTGAAG CTGATTTTCA AGGCTACTTA AAAAAATCTG      900
CAGCGTACAT TAATGGATTT CTGTTGTGTT TAAATTCTCC ACAGATTGTA TTGTAAATAT      960
TTATGAAGT AGAGCATATG TATATATTTA TATATACGTG CACATACATT AGTAGCACTA     1020
CCTTTGGAAG TCTCAGCTCT TGCTTTTCGG GACTGAAGCC AGTTTTGCAT GATAAAGTG     1080
GCCTTGTTAC GGGAGATAAT TGTGTTCTGT TGGGACTTTA GACAAAACTC ACCTGCAAAA     1140
AACTGACAGG CATTAACTAC TGGAACTTCC AAATAATGTG TTTGCTGATC GTTTACTCT     1200
TCGCATAAAT ATTTTAGGAA GTGTATGAGA ATTTTGCCTT CAGGAACTTT TCTAACAGCC     1260
AAAGACAGAA CTTAACCTCT GCAAGCAAGA TTCGTGGAAG ATAGTCTCCA CTTTTTAATG     1320
CACTAAGCAA TCGGTTGCTA GGAGCCCATC CTGGGTCAGA GGCCGATCCG CAGAACCAGA     1380
ACGTTTTCCC CTCCTGGACT GTTAGTAACT TAGTCTCCCT CCTCCCCTAA CCACCCCCGC     1440
CCCCCCCCAC CCCCCGCAGT AATAAAGGCC CCTGAACGTG TATGTTGGTC TCCCGGGAGC     1500
TGCTTGCTGA AGATCCGCGC CCCTGTCGCC GTCTGGTAGG AGCTGTTTGC AGGGTCCTAA     1560
CTCAATCGGC TTGTTGTG ATG CGT ATC CCC GTA GAT GCC AGC ACG AGC CGC       1611
                    Met Arg Ile Pro Val Asp Ala Ser Thr Ser Arg
                     1            5                   10
CGC TTC ACG CCG CCT TCC ACC GCG CTG AGC CCA GGC AAG ATG AGC GAG       1659
Arg Phe Thr Pro Pro Ser Thr Ala Leu Ser Pro Gly Lys Met Ser Glu
             15                  20                  25
GCG TTG CCG CTG GGC GCC CCG GAC GCC GGC GCT GCC CTG GCC GGC AAG       1707
Ala Leu Pro Leu Gly Ala Pro Asp Ala Gly Ala Ala Leu Ala Gly Lys
                 30                  35                  40
CTG AGG AGC GGC GAC CGC AGC ATG GTG GAG GTG CTG GCC GAC CAC CCG       1755
Leu Arg Ser Gly Asp Arg Ser Met Val Glu Val Leu Ala Asp His Pro
         45                  50                  55
GGC GAG CTG GTG CGC ACC GAC AGC CCC AAC TTC CTC TGC TCC GTG CTG       1803
Gly Glu Leu Val Arg Thr Asp Ser Pro Asn Phe Leu Cys Ser Val Leu
 60                  65                  70                  75
CCT ACG CAC TGG CGC TGC AAC AAG ACC CTG CCC ATC GCT TTC AAG GTG       1851
Pro Thr His Trp Arg Cys Asn Lys Thr Leu Pro Ile Ala Phe Lys Val
                 80                  85                  90
GTG GCC CTA GGG GAT GTT CCA GAT GGC ACT CTG GTC ACT GTG ATG GCT       1899
Val Ala Leu Gly Asp Val Pro Asp Gly Thr Leu Val Thr Val Met Ala
                     95                 100                 105
GGC AAT GAT GAA AAC TAC TCG GCT GAG CTG AGA AAT GCT ACC GCA GCC       1947
Gly Asn Asp Glu Asn Tyr Ser Ala Glu Leu Arg Asn Ala Thr Ala Ala
                 110                 115                 120
ATG AAG AAC CAG GTT GCA AGA TTT AAT GAC CTC AGG TTT GTC GGT CGA       1995
Met Lys Asn Gln Val Ala Arg Phe Asn Asp Leu Arg Phe Val Gly Arg
 125                 130                 135
AGT GGA AGA GGG AAA AGC TTC ACT CTG ACC ATC ACT GTC TTC ACA AAC       2043
Ser Gly Arg Gly Lys Ser Phe Thr Leu Thr Ile Thr Val Phe Thr Asn
 140                 145                 150                 155
CCA CCG CAA GTC GCC ACC TAC CAC AGA GCC ATC AAA ATC ACA GTG GAT       2091
Pro Pro Gln Val Ala Thr Tyr His Arg Ala Ile Lys Ile Thr Val Asp
```

-continued

|     |     |     | 160 |     |     |     |     | 165 |     |     |     |     | 170 |     |     |      |
|-----|-----|-----|-----|-----|-----|-----|-----|-----|-----|-----|-----|-----|-----|-----|-----|------|
| GGG | CCC | CGA | GAA | CCT | CGA | AAT | CGT | ACT | GAG | AAG | CAC | TCC | ACA | ATG | CCA | 2139 |
| Gly | Pro | Arg | Glu | Pro | Arg | Asn | Arg | Thr | Glu | Lys | His | Ser | Thr | Met | Pro |      |
|     |     | 175 |     |     |     |     |     | 180 |     |     |     |     | 185 |     |     |      |
| GAC | TCA | CCT | GTG | GAT | GTG | AAG | ACG | CAA | TCT | AGG | CTG | ACT | CCT | CCA | ACA | 2187 |
| Asp | Ser | Pro | Val | Asp | Val | Lys | Thr | Gln | Ser | Arg | Leu | Thr | Pro | Pro | Thr |      |
|     |     | 190 |     |     |     |     |     | 195 |     |     |     |     | 200 |     |     |      |
| ATG | CCA | CCT | CCC | CCA | ACT | ACT | CAA | GGA | GCT | CCA | AGA | ACC | AGT | TCA | TTT | 2235 |
| Met | Pro | Pro | Pro | Pro | Thr | Thr | Gln | Gly | Ala | Pro | Arg | Thr | Ser | Ser | Phe |      |
|     | 205 |     |     |     |     | 210 |     |     |     |     | 215 |     |     |     |     |      |
| ACA | CCG | ACA | ACG | TTA | ACT | AAT | GGC | ACG | AGC | CAT | TCT | CCT | ACA | GCC | TTG | 2283 |
| Thr | Pro | Thr | Thr | Leu | Thr | Asn | Gly | Thr | Ser | His | Ser | Pro | Thr | Ala | Leu |      |
| 220 |     |     |     |     | 225 |     |     |     |     | 230 |     |     |     |     | 235 |      |
| AAT | GGC | GCC | CCC | TCA | CCA | CCC | AAT | GGC | TTC | AGC | AAT | GGG | CCT | TCC | TCT | 2331 |
| Asn | Gly | Ala | Pro | Ser | Pro | Pro | Asn | Gly | Phe | Ser | Asn | Gly | Pro | Ser | Ser |      |
|     |     |     |     | 240 |     |     |     |     | 245 |     |     |     |     | 250 |     |      |
| TCT | TCC | TCC | TCC | TCT | CTG | GCT | AAT | CAA | CAG | CTG | CCC | CCA | GCC | TGT | GGT | 2379 |
| Ser | Ser | Ser | Ser | Ser | Leu | Ala | Asn | Gln | Gln | Leu | Pro | Pro | Ala | Cys | Gly |      |
|     |     |     | 255 |     |     |     |     | 260 |     |     |     |     | 265 |     |     |      |
| GCC | AGG | CAA | CTC | AGC | AAG | CTG | AAA | AGG | TTC | CTT | ACT | ACC | CTG | CAG | CAG | 2427 |
| Ala | Arg | Gln | Leu | Ser | Lys | Leu | Lys | Arg | Phe | Leu | Thr | Thr | Leu | Gln | Gln |      |
|     |     | 270 |     |     |     |     | 275 |     |     |     |     | 280 |     |     |     |      |
| TTT | GGC | AAT | GAC | ATT | TCA | CCC | GAG | ATA | GGA | GAA | AGA | GTT | CGC | ACC | CTC | 2475 |
| Phe | Gly | Asn | Asp | Ile | Ser | Pro | Glu | Ile | Gly | Glu | Arg | Val | Arg | Thr | Leu |      |
|     | 285 |     |     |     |     | 290 |     |     |     |     | 295 |     |     |     |     |      |
| GTT | CTG | GGA | CTA | GTG | AAC | TCC | ACT | TTG | ACA | ATT | GAA | GAA | TTT | CAT | TCC | 2523 |
| Val | Leu | Gly | Leu | Val | Asn | Ser | Thr | Leu | Thr | Ile | Glu | Glu | Phe | His | Ser |      |
| 300 |     |     |     |     | 305 |     |     |     |     | 310 |     |     |     |     | 315 |      |
| AAA | CTG | CAA | GAA | GCT | ACT | AAC | TTC | CCA | CTG | AGA | CCT | TTT | GTC | ATC | CCA | 2571 |
| Lys | Leu | Gln | Glu | Ala | Thr | Asn | Phe | Pro | Leu | Arg | Pro | Phe | Val | Ile | Pro |      |
|     |     |     |     | 320 |     |     |     |     | 325 |     |     |     |     | 330 |     |      |
| TTT | TTG | AAG | GCC | AAC | TTG | CCC | CTG | CTG | CAG | CGT | GAG | CTC | CTC | CAC | TGC | 2619 |
| Phe | Leu | Lys | Ala | Asn | Leu | Pro | Leu | Leu | Gln | Arg | Glu | Leu | Leu | His | Cys |      |
|     |     |     | 335 |     |     |     |     | 340 |     |     |     |     | 345 |     |     |      |
| GCA | AGA | CTG | GCC | AAA | CAG | AAC | CCT | GCC | CAG | TAC | CTC | GCC | CAG | CAT | GAA | 2667 |
| Ala | Arg | Leu | Ala | Lys | Gln | Asn | Pro | Ala | Gln | Tyr | Leu | Ala | Gln | His | Glu |      |
|     |     | 350 |     |     |     |     | 355 |     |     |     |     | 360 |     |     |     |      |
| CAG | CTG | CTT | CTG | GAT | GCC | AGC | ACC | ACC | TCA | CCT | GTT | GAC | TCC | TCA | GAG | 2715 |
| Gln | Leu | Leu | Leu | Asp | Ala | Ser | Thr | Thr | Ser | Pro | Val | Asp | Ser | Ser | Glu |      |
|     | 365 |     |     |     |     | 370 |     |     |     |     | 375 |     |     |     |     |      |
| CTG | CTT | CTC | GAT | GTG | AAC | GAA | AAC | GGG | AAG | AGG | CGA | ACT | CCA | GAC | AGA | 2763 |
| Leu | Leu | Leu | Asp | Val | Asn | Glu | Asn | Gly | Lys | Arg | Arg | Thr | Pro | Asp | Arg |      |
| 380 |     |     |     |     | 385 |     |     |     |     | 390 |     |     |     |     | 395 |      |
| ACC | AAA | GAA | AAT | GGC | TTT | GAC | AGA | GAG | CCT | TTG | CAC | TCA | GAA | CAT | CCA | 2811 |
| Thr | Lys | Glu | Asn | Gly | Phe | Asp | Arg | Glu | Pro | Leu | His | Ser | Glu | His | Pro |      |
|     |     |     |     | 400 |     |     |     |     | 405 |     |     |     |     | 410 |     |      |
| AGC | AAG | CGA | CCA | TGC | ACT | ATT | AGC | CCA | GGC | CAG | CGG | TAC | AGT | CCA | AAT | 2859 |
| Ser | Lys | Arg | Pro | Cys | Thr | Ile | Ser | Pro | Gly | Gln | Arg | Tyr | Ser | Pro | Asn |      |
|     |     |     | 415 |     |     |     |     | 420 |     |     |     |     | 425 |     |     |      |
| AAC | GGC | TTA | TCC | TAC | CAG | CCC | AAT | GGC | CTG | CCT | CAC | CCT | ACC | CCA | CCT | 2907 |
| Asn | Gly | Leu | Ser | Tyr | Gln | Pro | Asn | Gly | Leu | Pro | His | Pro | Thr | Pro | Pro |      |
|     |     | 430 |     |     |     |     | 435 |     |     |     |     | 440 |     |     |     |      |
| CCA | CCT | CAG | CAT | TAC | CGT | TTG | GAT | GAT | ATG | GCC | ATT | GCC | CAC | CAC | TAC | 2955 |
| Pro | Pro | Gln | His | Tyr | Arg | Leu | Asp | Asp | Met | Ala | Ile | Ala | His | His | Tyr |      |
|     | 445 |     |     |     |     | 450 |     |     |     |     | 455 |     |     |     |     |      |
| AGG | GAC | TCC | TAT | CGA | CAC | CCC | AGC | CAC | AGG | GAC | CTC | AGG | GAC | AGA | AAC | 3003 |
| Arg | Asp | Ser | Tyr | Arg | His | Pro | Ser | His | Arg | Asp | Leu | Arg | Asp | Arg | Asn |      |
| 460 |     |     |     |     | 465 |     |     |     |     | 470 |     |     |     |     | 475 |      |
| AGA | CCT | ATG | GGG | TTG | CAT | GGC | ACA | CGT | CAA | GAA | GAA | ATG | ATT | GAT | CAC | 3051 |
| Arg | Pro | Met | Gly | Leu | His | Gly | Thr | Arg | Gln | Glu | Glu | Met | Ile | Asp | His |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 480 |     |     |     |     | 485 |     |     |     |     | 490 |      |
| AGA | CTA | ACA | GAC | AGA | GAA | TGG | GCA | GAA | GAG | TGG | AAA | CAT | CTT | GAC | CAT | 3099 |
| Arg | Leu | Thr | Asp | Arg | Glu | Trp | Ala | Glu | Glu | Trp | Lys | His | Leu | Asp | His |      |
|     |     |     | 495 |     |     |     |     | 500 |     |     |     |     | 505 |     |     |      |
| CTG | TTA | AAC | TGC | ATA | ATG | GAC | ATG | GTA | GAA | AAA | ACA | AGG | CGA | TCT | CTC | 3147 |
| Leu | Leu | Asn | Cys | Ile | Met | Asp | Met | Val | Glu | Lys | Thr | Arg | Arg | Ser | Leu |      |
|     |     | 510 |     |     |     |     | 515 |     |     |     |     | 520 |     |     |     |      |
| ACC | GTA | CTA | AGG | CGG | TGT | CAA | GAA | GCA | GAC | CGG | GAA | GAA | TTG | AAT | TAC | 3195 |
| Thr | Val | Leu | Arg | Arg | Cys | Gln | Glu | Ala | Asp | Arg | Glu | Glu | Leu | Asn | Tyr |      |
|     | 525 |     |     |     |     | 530 |     |     |     |     | 535 |     |     |     |     |      |
| TGG | ATC | CGG | CGG | TAC | AGT | GAC | GCC | GAG | GAC | TTA | AAA | AAA | GGT | GGC | GGC | 3243 |
| Trp | Ile | Arg | Arg | Tyr | Ser | Asp | Ala | Glu | Asp | Leu | Lys | Lys | Gly | Gly | Gly |      |
| 540 |     |     |     |     | 545 |     |     |     |     | 550 |     |     |     |     | 555 |      |
| AGT | AGC | AGC | AGC | CAC | TCT | AGG | CAG | CAG | AGT | CCC | GTC | AAC | CCA | GAC | CCA | 3291 |
| Ser | Ser | Ser | Ser | His | Ser | Arg | Gln | Gln | Ser | Pro | Val | Asn | Pro | Asp | Pro |      |
|     |     |     |     | 560 |     |     |     |     | 565 |     |     |     |     | 570 |     |      |
| GTT | GCA | CTA | GAC | GCG | CAT | CGG | GAA | TTC | CTT | CAC | AGG | CCT | GCG | TCT | GGA | 3339 |
| Val | Ala | Leu | Asp | Ala | His | Arg | Glu | Phe | Leu | His | Arg | Pro | Ala | Ser | Gly |      |
|     |     |     | 575 |     |     |     |     | 580 |     |     |     |     | 585 |     |     |      |
| TAC | GTG | CCA | GAG | GAG | ATC | TGG | AAG | AAA | GCT | GAG | GAG | GCC | GTC | AAT | GAG | 3387 |
| Tyr | Val | Pro | Glu | Glu | Ile | Trp | Lys | Lys | Ala | Glu | Glu | Ala | Val | Asn | Glu |      |
|     |     | 590 |     |     |     |     | 595 |     |     |     |     | 600 |     |     |     |      |
| GTG | AAG | CGC | CAG | GCG | ATG | ACG | GAG | CTG | CAG | AAG | GCC | GTG | TCT | GAG | GCG | 3435 |
| Val | Lys | Arg | Gln | Ala | Met | Thr | Glu | Leu | Gln | Lys | Ala | Val | Ser | Glu | Ala |      |
| 605 |     |     |     |     | 610 |     |     |     |     | 615 |     |     |     |     |     |      |
| GAG | CGG | AAA | GCC | CAC | GAC | ATG | ATC | ACA | ACA | GAG | AGG | GCC | AAG | ATG | GAG | 3483 |
| Glu | Arg | Lys | Ala | His | Asp | Met | Ile | Thr | Thr | Glu | Arg | Ala | Lys | Met | Glu |      |
| 620 |     |     |     |     | 625 |     |     |     |     | 630 |     |     |     |     | 635 |      |
| CGC | ACG | GTC | GCC | GAG | GCC | AAA | CGG | CAG | GCG | GCG | GAG | GAC | GCA | CTG | GCA | 3531 |
| Arg | Thr | Val | Ala | Glu | Ala | Lys | Arg | Gln | Ala | Ala | Glu | Asp | Ala | Leu | Ala |      |
|     |     |     |     | 640 |     |     |     |     | 645 |     |     |     |     | 650 |     |      |
| GTT | ATC | AAT | CAG | CAG | GAG | GAT | TCA | AGC | GAG | AGT | TGC | TGG | AAT | TGT | GGC | 3579 |
| Val | Ile | Asn | Gln | Gln | Glu | Asp | Ser | Ser | Glu | Ser | Cys | Trp | Asn | Cys | Gly |      |
|     |     |     | 655 |     |     |     |     | 660 |     |     |     |     | 665 |     |     |      |
| CGT | AAA | GCG | AGT | GAA | ACC | TGC | AGT | GGC | TGT | AAC | ACA | GCC | CGA | TAC | TGT | 3627 |
| Arg | Lys | Ala | Ser | Glu | Thr | Cys | Ser | Gly | Cys | Asn | Thr | Ala | Arg | Tyr | Cys |      |
|     |     | 670 |     |     |     |     | 675 |     |     |     |     | 680 |     |     |     |      |
| GGC | TCA | TTT | TGC | CAG | CAC | AAA | GAC | TGG | GAG | AAG | CAC | CAT | CAC | ATC | TGT | 3675 |
| Gly | Ser | Phe | Cys | Gln | His | Lys | Asp | Trp | Glu | Lys | His | His | His | Ile | Cys |      |
|     | 685 |     |     |     |     | 690 |     |     |     |     | 695 |     |     |     |     |      |
| GGA | CAG | ACC | CTG | CAG | GCC | CAG | CAG | CAG | GGA | GAC | ACA | CCT | GCA | GTC | AGC | 3723 |
| Gly | Gln | Thr | Leu | Gln | Ala | Gln | Gln | Gln | Gly | Asp | Thr | Pro | Ala | Val | Ser |      |
| 700 |     |     |     |     | 705 |     |     |     |     | 710 |     |     |     |     | 715 |      |
| TCC | TCT | GTC | ACG | CCC | AAC | AGC | GGG | GCT | GGG | AGC | CCG | ATG | GAC | ACA | CCA | 3771 |
| Ser | Ser | Val | Thr | Pro | Asn | Ser | Gly | Ala | Gly | Ser | Pro | Met | Asp | Thr | Pro |      |
|     |     |     |     | 720 |     |     |     |     | 725 |     |     |     |     | 730 |     |      |
| CCA | GCA | GCC | ACT | CCG | AGG | TCA | ACC | ACC | CCG | GGA | ACC | CCT | TCC | ACC | ATA | 3819 |
| Pro | Ala | Ala | Thr | Pro | Arg | Ser | Thr | Thr | Pro | Gly | Thr | Pro | Ser | Thr | Ile |      |
|     |     |     | 735 |     |     |     |     | 740 |     |     |     |     | 745 |     |     |      |
| GAG | ACA | ACC | CCT | CGC | TAGACGTGAA | CTCAGAACTG | TCGGAGGAAA | GACAACACAA |     |     |     |     |     |     |     | 3874 |
| Glu | Thr | Thr | Pro | Arg |     |     |     |     |     |     |     |     |     |     |     |      |
|     |     |     | 750 |     |     |     |     |     |     |     |     |     |     |     |     |      |

```
CCAACGCGAA ACCAATTCCT CATCCTCAGA TGCTCAAAGT TGTTTTTTTT GTTTGTTTGT    3934
TTATTAGATG AATTATCCTA TTTCAGTACT TCAGCAAGAG AGAACCTAAC TGTATCTTGA    3994
GGTGGTAGTA AAACACAGAG GGCCAGTAAC GGGTCGTAAT GACTTATTGT GGATAACAAA    4054
GATATCTTTT CTTTAGAGAA CTGAAAAGAG AGCAGAGAAT ATAACATGAA ATGATAGATT    4114
TGACCTCCTC CCTGTTATTT TCAAGTAGCT GGGATTTTAA ACTAGATGAC CTCATTAACC    4174
```

```
GATGCTTTAC CAAACAGCAA ACCAAGAGAT TGCTAATTGC TGTTGAAAGC AAAAATGCTA        4234

ATATTAAAAG TCACAATGTT CTTTATATAC AATAATGGAA AAAAAAAAAA AAA             4287
```

( 2 ) INFORMATION FOR SEQ ID NO:2:

( i ) SEQUENCE CHARACTERISTICS:
        ( A ) LENGTH: 752 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Ile  Pro  Val  Asp  Ala  Ser  Thr  Ser  Arg  Arg  Phe  Thr  Pro  Pro
 1              5                        10                       15

Ser  Thr  Ala  Leu  Ser  Pro  Gly  Lys  Met  Ser  Glu  Ala  Leu  Pro  Leu  Gly
              20                       25                       30

Ala  Pro  Asp  Ala  Gly  Ala  Ala  Leu  Ala  Gly  Lys  Leu  Arg  Ser  Gly  Asp
         35                       40                       45

Arg  Ser  Met  Val  Glu  Val  Leu  Ala  Asp  His  Pro  Gly  Glu  Leu  Val  Arg
    50                       55                       60

Thr  Asp  Ser  Pro  Asn  Phe  Leu  Cys  Ser  Val  Leu  Pro  Thr  His  Trp  Arg
65                       70                       75                       80

Cys  Asn  Lys  Thr  Leu  Pro  Ile  Ala  Phe  Lys  Val  Val  Ala  Leu  Gly  Asp
                   85                       90                       95

Val  Pro  Asp  Gly  Thr  Leu  Val  Thr  Val  Met  Ala  Gly  Asn  Asp  Glu  Asn
              100                      105                      110

Tyr  Ser  Ala  Glu  Leu  Arg  Asn  Ala  Thr  Ala  Ala  Met  Lys  Asn  Gln  Val
         115                      120                      125

Ala  Arg  Phe  Asn  Asp  Leu  Arg  Phe  Val  Gly  Arg  Ser  Gly  Arg  Gly  Lys
    130                      135                      140

Ser  Phe  Thr  Leu  Thr  Ile  Thr  Val  Phe  Thr  Asn  Pro  Pro  Gln  Val  Ala
145                      150                      155                      160

Thr  Tyr  His  Arg  Ala  Ile  Lys  Ile  Thr  Val  Asp  Gly  Pro  Arg  Glu  Pro
                   165                      170                      175

Arg  Asn  Arg  Thr  Glu  Lys  His  Ser  Thr  Met  Pro  Asp  Ser  Pro  Val  Asp
              180                      185                      190

Val  Lys  Thr  Gln  Ser  Arg  Leu  Thr  Pro  Pro  Thr  Met  Pro  Pro  Pro  Pro
         195                      200                      205

Thr  Thr  Gln  Gly  Ala  Pro  Arg  Thr  Ser  Ser  Phe  Thr  Pro  Thr  Thr  Leu
    210                      215                      220

Thr  Asn  Gly  Thr  Ser  His  Ser  Pro  Thr  Ala  Leu  Asn  Gly  Ala  Pro  Ser
225                      230                      235                      240

Pro  Pro  Asn  Gly  Phe  Ser  Asn  Gly  Pro  Ser  Ser  Ser  Ser  Ser  Ser  Ser
                   245                      250                      255

Leu  Ala  Asn  Gln  Gln  Leu  Pro  Pro  Ala  Cys  Gly  Ala  Arg  Gln  Leu  Ser
              260                      265                      270

Lys  Leu  Lys  Arg  Phe  Leu  Thr  Thr  Leu  Gln  Gln  Phe  Gly  Asn  Asp  Ile
         275                      280                      285

Ser  Pro  Glu  Ile  Gly  Glu  Arg  Val  Arg  Thr  Leu  Val  Leu  Gly  Leu  Val
    290                      295                      300

Asn  Ser  Thr  Leu  Thr  Ile  Glu  Glu  Phe  His  Ser  Lys  Leu  Gln  Glu  Ala
305                      310                      315                      320

Thr  Asn  Phe  Pro  Leu  Arg  Pro  Phe  Val  Ile  Pro  Phe  Leu  Lys  Ala  Asn
                   325                      330                      335

Leu  Pro  Leu  Leu  Gln  Arg  Glu  Leu  Leu  His  Cys  Ala  Arg  Leu  Ala  Lys
```

|       |       |       | 340   |       |       | 345   |       |       |       | 350   |       |       |
|-------|-------|-------|-------|-------|-------|-------|-------|-------|-------|-------|-------|-------|
| Gln   | Asn   | Pro   | Ala   | Gln   | Tyr   | Leu   | Ala   | Gln   | His   | Glu   | Gln   | Leu   | Leu   | Leu   | Asp   |
|       |       | 355   |       |       |       | 360   |       |       |       |       | 365   |       |       |       |       |

Ala Ser Thr Thr Ser Pro Val Asp Ser Ser Glu Leu Leu Leu Asp Val
370 375 380

Asn Glu Asn Gly Lys Arg Arg Thr Pro Asp Arg Thr Lys Glu Asn Gly
385 390 395 400

Phe Asp Arg Glu Pro Leu His Ser Glu His Pro Ser Lys Arg Pro Cys
405 410 415

Thr Ile Ser Pro Gly Gln Arg Tyr Ser Pro Asn Asn Gly Leu Ser Tyr
420 425 430

Gln Pro Asn Gly Leu Pro His Pro Thr Pro Pro Pro Gln His Tyr
435 440 445

Arg Leu Asp Asp Met Ala Ile Ala His His Tyr Arg Asp Ser Tyr Arg
450 455 460

His Pro Ser His Arg Asp Leu Arg Asp Arg Asn Arg Pro Met Gly Leu
465 470 475 480

His Gly Thr Arg Gln Glu Glu Met Ile Asp His Arg Leu Thr Asp Arg
485 490 495

Glu Trp Ala Glu Glu Trp Lys His Leu Asp His Leu Leu Asn Cys Ile
500 505 510

Met Asp Met Val Glu Lys Thr Arg Arg Ser Leu Thr Val Leu Arg Arg
515 520 525

Cys Gln Glu Ala Asp Arg Glu Glu Leu Asn Tyr Trp Ile Arg Arg Tyr
530 535 540

Ser Asp Ala Glu Asp Leu Lys Lys Gly Gly Gly Ser Ser Ser Ser His
545 550 555 560

Ser Arg Gln Gln Ser Pro Val Asn Pro Asp Pro Val Ala Leu Asp Ala
565 570 575

His Arg Glu Phe Leu His Arg Pro Ala Ser Gly Tyr Val Pro Glu Glu
580 585 590

Ile Trp Lys Lys Ala Glu Glu Val Asn Glu Val Lys Arg Gln Ala
595 600 605

Met Thr Glu Leu Gln Lys Ala Val Ser Glu Ala Glu Arg Lys Ala His
610 615 620

Asp Met Ile Thr Thr Glu Arg Ala Lys Met Glu Arg Thr Val Ala Glu
625 630 635 640

Ala Lys Arg Gln Ala Ala Glu Asp Ala Leu Ala Val Ile Asn Gln Gln
645 650 655

Glu Asp Ser Ser Glu Ser Cys Trp Asn Cys Gly Arg Lys Ala Ser Glu
660 665 670

Thr Cys Ser Gly Cys Asn Thr Ala Arg Tyr Cys Gly Ser Phe Cys Gln
675 680 685

His Lys Asp Trp Glu Lys His His His Ile Cys Gly Gln Thr Leu Gln
690 695 700

Ala Gln Gln Gln Gly Asp Thr Pro Ala Val Ser Ser Ser Val Thr Pro
705 710 715 720

Asn Ser Gly Ala Gly Ser Pro Met Asp Thr Pro Pro Ala Ala Thr Pro
725 730 735

Arg Ser Thr Thr Pro Gly Thr Pro Ser Thr Ile Glu Thr Thr Pro Arg
740 745 750

( 2 ) INFORMATION FOR SEQ ID NO:3:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc ="PCR primer"

(iii) HYPOTHETICAL: NO (iv) ANTI-SENSE: NO (xi) SEQUENCE DESCRIPTION: SEQ ID NO:3:

GAGGGAAAAG CTTCACTCTG                      20

(2) INFORMATION FOR SEQ ID NO:4:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="PCR primer"

(iii) HYPOTHETICAL: NO (iv) ANTI-SENSE: NO (xi) SEQUENCE DESCRIPTION: SEQ ID NO:4:

GCGAACTCTT TCTCCTATC                       19

AML1-MTG8 FUSION PROTEIN RESULTING FROM T(8;21) TRANSLOCATION IN ACUTE MYELOID LEUKEMIA

TECHNICAL FIELD

The present invention relates to novel DNAs, polypeptides encoded thereby and methods for detecting the DNAs and the polypeptides. The present invention is useful for diagnosis of t(8;21) translocation type acute myeloid leukemia.

BACKGROUND ART

The t(8;21) translocation type acute myeloid leukemia is an acute myeloid leukemia (hereinafter also referred to as "AML") which accompanies translocation of a gene on chromosome 8 to chromosome 21, which is one the most frequent acute myeloid leukemias ranking with t(15;17) translocation type acute myeloid leukemia. The t(8;21)(q22;q22) translocation type acute myeloid leukemia morphologically associates with FAB-M2 subtype of AML (Fourth International Workshop on Chromosomes in Leukemia, 1982, *Cancer Genet. Cytogenet.* 11, 284 (1984); J. D. Rowley, Sem. Hematol. 27, 122 (1990)). Leukemic cells with the t(8;21) translocation are uniquely characterized by a high frequency of Auer rods and mutation of granulocytic line (R. Berger et al., Blood 59, 171 (1982)). Cytogenetically, this translocation is often accompanied by a loss of sex chromosome which is rarely observed in acute leukemias without t(8;21) translocation.

Diagnosis of t(8;21) translocation type AML can be attained by detecting the above-mentioned features or by analyzing the chromosomes. However, these methods are troublesome and the sensitivity of the diagnosis is not satisfactory.

DISCLOSURE OF THE INVENTION

Accordingly, an object of the present invention is to provide means for diagnosing t(8;21) translocation type acute myeloid leukemia by a simple operation with high sensitivity.

As a result of intensive study, the present inventors discovered that a transcript of a fused gene of AML1 gene (H. Miyoshi et al., Proc. Natl. Acad. Sci. U.S.A. 8, 10431 (1991)) on chromosome 21 and an unknown gene neighboring the AML1 gene exists, the unknown gene being translocated from chromosome 8. The present inventors also succeeded in determining the nucleotide sequence of the fused gene. The present inventors further discovered a method for diagnosing t(8;21) translocation type AML by specifically detecting the fused gene or the transcript thereof, thereby completing the present invention.

That is, the present invention provides AML1-MTG8 fused DNA having the nucleotide sequence shown in SEQ ID No. 1 and DNA fragments thereof containing the fused site. It should be noted that we named the unknown gene on chromosome 8 MTG8, which gene adjoins to the AML1 gene on chromosome 21 in t(8;21) translocation.

The present invention also provides AML1-MTG8 fused polypeptide having the amino acid sequence shown in SEQ ID No. 2 and fragments thereof containing the fused site.

The present invention further provides AML1-MTG8 fused mRNA having the same nucleotide sequence as shown in SEQ ID No. 1 except that thymine is replaced with uracil, and fragments thereof.

The present invention still further provides probes which are said DNA fragments that are labelled, and methods for detecting the fused DNA by using the probes.

The present invention still further provides probes which are DNAs or RNAs that are complementary to said fused mRNA or fragments thereof, the DNAs or RNAs being labelled, as well as methods for detecting the mRNA using the probes.

The present invention still further provides methods for detecting AML1-MTG8 fused DNA or a fragment thereof in a sample, comprising the steps of amplifying said fused DNA or a fragment thereof by a nucleic acid-amplifying method and detecting the amplified DNA fragment.

The present invention still further provides methods for detecting AML1-MTG8 fused mRNA or a fragment thereof in a sample, comprising the steps of amplifying said fused mRNA according to the present invention or a fragment thereof by a nucleic acid-amplifying method and detecting the amplified RNA fragment.

The present invention still further provides methods for detecting the polypeptide according to the present invention by an immunoassay employing an antibody specific to the polypeptide.

By the present invention, a fused DNA which is specifically generated in t(8;21) translocation type AML and fragments thereof and a polypeptide encoded thereby and fragments thereof, as well as methods for detecting them were provided. By the present invention, it was first possible to diagnose t(8;21) translocation type AML specifically with high sensitivity by a simple operation.

BEST MODE FOR CARRYING OUT THE INVENTION

The nucleotide sequence of AML1-MTG8 fused DNA was determined by extracting total RNAs of bone marrow cells of a t(8;21) translocation type AML patient, preparing a cDNA library therefrom, screening the obtained cDNA library with a probe specific to AML1 gene (H. Miyoshi et al., supra), and by determining the nucleotide sequence of the DNA detected by the probe. For confirmation, a probe specific to the MTG8 moiety was prepared and a similar screening using this probe and the probe specific to AML1 gene was carried out. Further, cDNAs were prepared from the RNAs from a t(8;21) translocation type AML patient, a DNA fragment containing the fused site of the cDNA was amplified by PCR method depending on the information of the determined nucleotide sequence, and the amplified DNA fragment was detected, thereby confirming that the diagnosis of t(8;21) translocation type AML can be attained by the above-mentioned procedures. Thus, it was confirmed that the DNA according to the present invention is the AML1-MTG8 fused DNA characteristic to t(8;21) translocation type AML. The details of the above-mentioned procedures are described in Example 1 below.

The DNA according to the present invention, the nucleotide sequence of which was determined as mentioned above, has the nucleotide sequence shown in SEQ ID No. 1. By comparing this nucleotide sequence with the AML1 gene on chromosome 21, it is seen that the nucleotide sequence up to the 2110th base adenine is exactly the same as that of the AML1 gene and the nucleotide sequence after the 2110th nucleotide is not hitherto known, which is assumed to be a gene translocated from chromosome 8. As mentioned above, since this gene was named MTG8, the DNA can be called AML1-MTG8 fused DNA. It should be noted that in the present specification, the term "fused site" means the site between the 2110th base adenine and the 2111th base adenine. The deduced amino acid sequence encoded by the above-mentioned fused DNA is also shown in SEQ ID No. 1. In the polypeptide having this amino acid sequence, the term "fused site" means the site between the 177th amino acid arginine and the 178th amino acid aspargine.

The fused DNA according to the present invention may be prepared by the method detailed in the Example described below. Alternatively, the fused DNA according to the present invention may be easily prepared by a nucleic acid-amplifying method such as PCR method using the bone marrow cells from a t(8;21) translocation type AML patient, based on the information of the nucleotide sequence shown in SEQ ID No. 1.

Needless to say the DNA having the entire nucleotide sequence shown in SEQ ID No. 1, fragments of this DNA which contain the fused site of the nucleotide sequence are also within the scope of the present invention. This is because the fused site is characteristic to t(8;21) translocation type AML, the DNA fragments containing the fused site are useful for the diagnosis of t(8;21) translocation type AML even if they do not have the full length. Arbitrary DNA fragments containing the fused site can be prepared by a nucleic acid-amplifying method such as PCR method using the bone marrow cells from a t(8;21) translocation type AML patient, based on the information of the nucleotide sequence shown in SEQ ID No. 1. Similarly, as for the polypeptide encoded by the AML1-MTG8 fused DNA according to the present invention, in addition to the polypeptide having the entire amino acid sequence shown in SEQ ID No. 2, fragments thereof containing the fused site are also within the scope of the present invention. The polypeptide can be easily prepared by recombining the fused DNA according to the present invention in a vector by a conventional method and expressing the obtained recombinant vector in a host cell.

Since the above-mentioned fused DNA according to the present invention was obtained by using mRNAs in bone marrow cells of a t(8;21) translocation type AML patient as a starting material, it is apparent that AML1-MTG8 fused mRNA which has the same nucleotide sequence as shown in SEQ ID NO. 1 except that thymine is substituted by uracil does exist. The present invention also provides such a mRNA and fragments thereof containing the fused site. Such a mRNA and fragments thereof can be obtained by the method detailed in Example 1 described below. Alternatively, since the nucleotide sequence of the mRNA has been determined and since mRNA itself can be amplified by a nucleic acid-amplifying method such as 3SR method (Japanese Laid-open PCT Application (Kohyo) No. 2-500565) or NASBA method (Japanese Laid-open Patent Application (Kokai) No. 2-005864), optional mRNA fragments can be obtained using bone marrow cells from a t(8;21) translocation type AML patient as a starting material.

The fused site in the above-described DNAs, polypeptides or mRNAs is characteristic to t(8;21) translocation type AML. Since AML1 gene and MTG8 gene exist on chromosome 21 and chromosome 8, respectively, in normal cells and cells of patients suffering from other translocation type AMLs, diagnosis of t(8;21) translocation type AML cannot be attained even if these genes are detected separately. However, since the above-mentioned fused site does not exist in normal cells and in cells of patients suffering from other translocation type AMLs, but exists only in the cells of patients suffering from t(8;21) translocation type, t(8;21) translocation type AML can be specifically diagnosed by detecting the fused site.

As means for detecting the fused site, the present invention first provides a probe which is the above-described fused DNA or a fragment thereof containing the fused site, the fused DNA or the fragment thereof being labelled. The present invention also provides a probe which is a labelled DNA or RNA complementary to the above-described fused mRNA or a fragment thereof containing the fused site. By checking whether the sequence complementary to the probe exists or not, that is, whether the fused DNA or the fused mRNA exists or not by using the above-mentioned probe, it can be determined whether the fused site exists in the cells or not, and in turn, whether the patient suffers from t(8;21) translocation type AML or not. The method for labelling a probe is well-known in the art.

Since the nucleotide sequence shown in SEQ ID No. 1 was determined according to the present invention, the detection of the fused DNA shown in SEQ ID No. 1 or the fused mRNA, and in turn, diagnosis of t(8;21) translocation type AML can be attained by amplifying the entire fused DNA or a fragment thereof containing the fused site, or the entire fused mRNA or a fragment thereof containing the fused site by a nucleic acid-amplifying method based on the information of the determined nucleotide sequence, and detecting the amplified nucleic acid fragment by staining with ethidium bromide or the like after electrophoresing the amplified nucleic acid fragment. In Example 2 described below, diagnosis of t(8;21) translocation type AML was attained by amplifying the sequence from the 2004th base guanine to the 2468th base cytosine by PCR method by using the sequence from the 2004th base guanine to the 2023rd base guanine as a primer 1 and using the sequence complementary to the sequence from the 2468th base cytosine to the 2451st base guanine as a primer 2 (antisense). The region to be amplified is not restricted to that described in Example 2 below but any region which spans the fused site may be amplified. This method has extremely high sensitivity and if one cell having the t(8;21) translocation exists in $10^8$ cells, the t(8;21) translocation can be detected.

Since the fused DNA according to the present invention was prepared from a mRNA in bone marrow cells of t(8;21) translocation type AML patient, the fused DNA is thought to be expressed in cells to produce a polypeptide encoded by the DNA. Therefore, by preparing an antibody, preferably a monoclonal antibody, specific to the polypeptide or a fragment thereof containing the fused site by a conventional method, and by specifically detecting the polypeptide using the antibody by an immunoassay, the t(8;21) translocation type AML can be diagnosed.

The present invention will now be described by way of examples thereof. It should be noted, however, that the present invention is not restricted to the examples.

EXAMPLE 1

Isolation of AML1-MTG8 Fused DNA

1. Extraction and Isolation of RNAs

From an acute myeloid leukemia cell line Kasumi-1 (H. Asou et al., Blood, 77, 2031 (1991)), RNAs were isolated by AGPC method (Chomczynski et al., Anal. Biochem. 162, 156–159 (1987)). This method will now be described.

1) Kasumi-1 cells are collected by centrifugation as a precipitate and 1 ml of Solution D (4M guanidine thiocyanate, 25 mM sodium citrate, 0.5% sarcosine and 0.1M 2-mercaptoethanol) is added per $10^7$ cells to solubilize the cells in Solution D.

2) The following reagents were added sequentially and the mixture is mixed each time the next reagent is added.

2M sodium acetate (pH 4.0) 1/10 volume water-saturated phenol equivolume chloroform/isoamyl alcohol (49:1) 1/5 volume 3) The resulting mixture is vigorously shaken for 10 seconds and cooled in ice for 15 minutes 4) The resulting mixture is transferred to a centrifugal tube and centrifuged at 4° C., 10,000× g for 20 minutes.

5) The aqueous layer is transferred to another centrifugal tube, equivolume isopropanol is added and the resulting mixture is mixed well.

6) The mixture is left to stand at −20° C. for 1 hour.

7) The resultant is centrifuged at 4° C., 10,000× g for 20 minutes.

8) The supernatant is discarded and Solution D is added to the precipitate of RNAs in an amount of 0.1 ml per $10^7$ cells. To the resulting solution, equivolume of isopropanol is added and the resultant mixture is mixed well.

9) The resulting mixture is left to stand at −20° C. for 1 hour.

10) The resultant mixture is centrifuged at 4° C., 10,000× g for 10 minutes.

11) The supernatant is discarded and the precipitate of RNAs is washed with 75% ethanol, followed by drying the precipitate.

12) The obtained precipitate is dissolved in appropriate amount of DEPC-treated distilled water.

Poly(A)$^+$ RNA was isolated from the thus isolated RNAs by using Oligotex-dT30 (NIPPON ROCHE) in accordance with the protocol of the commercial product.

2. Preparation of cDNA Library

Using about 5 μg of the poly(A)$^+$ RNA purified from Kasumi-1 cells, a cDNA library was prepared by the following operations:

1) About 5 μg of poly(A)$^+$ RNA and 2.5 μg of oligo d(T)$_{12-18}$ (PHARMACIA) are heated at 70° C. for 10 minutes in DEPC-treated distilled water, and the resultant is then cooled in ice.

2) Fifty microliters of a reaction mixture (50 mM Tris-HCl (pH 8.3), 40 mM KCl, 10 mM DTT, 6 mM MgCl$_2$ and 0.5 mM dNTP) is prepared, and 40 units of RNase inhibitor (commercially available from BOEHRINGER) and 500 units of M-MLV H$^−$ reverse transcriptase (BRL) are added thereto. The mixture is then incubated at 37° C. for 1 hour to synthesize ss-cDNA.

3) Four hundred microliters of a reaction mixture (20 mM Tris-HCl (pH 6.9), 90 mM KCl, 5 mM MgCl$_2$, 0.15 mM β-NAD, 10 mM (NH$_4$)$_2$SO$_4$, 5 mM DTT and 0.25 mM dNTP) is prepared, and 30 units of *E. coli* DNA ligase (NEB), 40 units of *E. coli* DNA polymerase I and 4 units of *E. coli* RNaseH (BRL) are added thereto. The resulting mixture is incubated at 16° C. for 2 hours and 10 units of T4 DNA polymerase (BRL) is added thereto, followed by incubating the resultant at 37° C. for 15 minutes to synthesize ds-cDNAs.

4) Sixteen microliters of 0.5M EDTA (pH 8.0) is added to the resulting mixture.

5) The resultant is extracted with 400 μl of phenol/chloroform mixture.

6) The resultant is extracted with 400 μl of chloroform.

7) 1/10 volume of 3M sodium acetate (pH 5.2) and 2.5 times volume of ethanol are added and the resultant is centrifuged to recover ds-cDNAs as a precipitate.

8) EcoRI/NotI adaptor (PHARMACIA) and 400 units of T4 DNA ligase (NEB) are added and the resulting mixture is allowed to react at 16° C. for 16 hours to ligate the ds-cDNAs with the adaptor.

9) The resultant is reacted with 20 units of T4 polynucleotide kinase (BRL) at 37° C. for 30 minutes to carry out phospholylation.

10) The resultant is incubated at 65° C. for 10 minutes.

11) The steps 5)–7) are repeated.

12) The cDNAs are fractionated by density gradient centrifugation in potassium acetate and fractions of cDNAs of not less than 2 kb are collected.

13) The cDNAs are digested with restriction enzyme EcoRI, and 1 μg of λ ZAP II vector (STRATAGENE) and 200 units of T4 DNA ligase (NEB) are added. The resultant is allowed to react overnight at 16° C.

14) The reaction mixture is subjected to packaging using GIGAPACK II PACKAGING EXTRACTS (STRATAGENE) and λ plaques in *E. coli* XL1-Blue as a host, thereby preparing a library.

3. Screening of Fused Gene cDNA

Screening of the cDNA library comprising about 1,000,000 plaques was carried out as follows:

1) A library is prepared using plates with a diameter of about 15 cm and the number of plaques on one plate is adjusted to 40,000 to 50,000.

2) On each plate in which plaques are formed, a nylon membrane HYBOND-N (AMERSHAM) is placed and left to stand for 1 minute.

3) The nylon membrane is gently peeled off from the plate and immersed in a denaturing solution (0.5N NaOH, 1.5M NaCl) for 5 minutes.

4) The membrane is immersed in a neutralization solution (0.5M Tris-HCl (pH 7.5), 1.5M NaCl) for 5 minutes.

5) The membrane is washed with 2×SSC (1×SSC: 0.15M NaCl, 15 mM sodium citrate) and dried in the air. The nylon membrane is then irradiated with U.V. with a wavelength of 312 nm to fix DNAs on the membrane.

6) AML1 cDNA probe (C6E6H2, (H. Miyoshi et al., supra) or a part of CH15 clone isolated by RT/PCR method (CH15H2S, 2247–2701 bases) is labelled with $^{32}$p by using a multiprime labelling kit (AMERSHAM) and then boiled and rapidly cooled to denature the probe.

7) The labelled probe and the nylon membrane are incubated in a hybridization solution (6×SSC, 10% dextran sulfate, 1% SDS, 1× Denhart's solution, 50% formamide) at 42° C. overnight to carry out hybridization.

8) The membrane is washed with 2× SSC, 1% SDS solution.

9) The membrane is washed with 0.1× SSC, 0.1% SDS solution at 65° C. for 1 hour.

10) The membrane is sandwiched between SARAN WRAP (trademark) and the resultant is laminated on an X-ray film, followed by conducting autoradiography.

11) Phage DNAs of positive clones are purified.

12) The phage DNAs are digested with restriction enzyme Not I and the insert regions are recloned to Not I site of pBluescript II KS$^+$ (STRATAGENE).

4. Determination of DNA Sequence

The nucleotide sequence of the cDNA insert recloned in pBluescript II KS$^+$ (PHARMACIA) was determined using A.L.F. DNA SEQUENCER (PHARMACIA). All of the experimental procedures and reactions were in accordance with the protocol instructed by PHARMACIA.

EXAMPLE 2

Diagnosis of t(8;21) Translocation Type Myeloid Leukemia by RT-PCR Method and Detection of Minimal Residual Disease—Example 1. Reverse Transcription Reaction Using 1–5 μg of total RNAs from bone marrow cells of a leukemia patient, cDNAs were prepared by using a reverse transcriptase. The composition of the reaction solution (20

μg) is as follows: 10 mM Tris-HCl (pH 8.3), 75 mM potassium chloride, 3 mM magnesium chloride, 1 mM dithiothreitol, 1 mM dATP, 1 mM dGTP, 1 mM dCTP, 1 mM dTTP, 10 units of RNase inhibitor, 25 pmol of random hexamer, 200 units of reverse transcriptase and 1–5 μg of RNAs. The reaction mixture was left to stand at room temperature for 10 minutes to anneal the primers with the template RNAs, and the resultant was allowed to react at 37° C. for 1 hour. After the reaction, the mixture was heated at 99° C. for 5 minutes to inactivate the reverse transcriptase and to dissociate the generated cDNAs from the template RNAs.

2. PCR

Using 1/10 volume (2 μl) of the reverse transcripts (cDNAs), a primer AML1-C which has a sequence of a part of AML1 gene and a primer MTG8-2 which has a sequence of a part of MTG8 gene, a sequence in the vicinity of the fused site of the t(8;21) transcript was amplified by using a thermostable DNA polymerase. The composition of the PCR solution (25 μl) is as follows: 10 mM Tris-HCl (pH 8.3), 50 mM potassium chloride, 3 mM magnesium chloride, 0.2 mM dATP, 0.2 mM dGTP, 0.2 mM dCTP, 0.2 mM TTP, 5 pmol AML1-C (5'-GAGGGAAAAGCTTCACTCTG-3'), (SEQ. I.D. No. 3), 5 pmol MTG8-2 (5'-GCGAACTCTTTCTCCTATC-3') (SEQ. I.D. No. 4) and 1.25 units of Taq DNA polymerase. To prevent evaporation of the reaction solution, one drop of liquid paraffin was overlaid. After denaturing the DNAs at 95° C. for 2 minutes, a cycle of annealing step at 62° C. for 30 seconds, extension step at 72° C. for 1 minute and thermal denaturing step at 95° C. for 20 seconds was repeated 34 times using an automatic PCR apparatus. After completion of the 34 cycles, annealing step at 62° C. for 30 seconds and extension step at 72° C. for 7 minutes were carried out.

3. Analysis of Product Amplified by PCR

After the PCR, 1/5 volume of 6× loading buffer (containing 30% glycerol, 0.25% Bromphenol Blue, 0.25% xylenecyanol was added and the mixture was well stirred well. Half of the resultant was subjected to 3% Nusieve 3:1 agarose gel electrophoresis. The electrophoresis was performed in a buffer solution containing 0.5 μg/ml of ethidium bromide. After the electrophoresis, the gel was irradiated with U.V. and a DNA product stained with ethidium bromide was detected. When AML1-C and MTG8-2 are used as primers, the amplification of DNA of 457 bp indicated the t(8;21) translocation. By this method, diagnosis of t(8;21) translocation type AML was attained with high sensitivity.

Industrial Availability

As described above, by the present invention, specific diagnosis of t(8;21) translocation type AML was attained with high sensitivity by simple operations. Therefore, the present invention is useful for diagnosis of t(8;21) translocation type AML.

We claim:

1. Isolated and purified AML1-MTG8 fused DNA comprising the contiguous nucleotide sequence consisting of SEQ ID No. 1.

2. An isolated and purified DNA fragment comprising contiguous nucleotides on the 5' and 3' side of the fused site of AML1-MTG8 fused DNA, said fused site being the site between bases 2110 and 2111 of the nucleotide sequence of SEQ ID No. 1, wherein said DNA fragment specifically hybridizes with said nucleotide sequence consisting of SEQ. ID. NO. 1 but does not specifically hybridize with AML1 DNA or MTG8 DNA.

3. Isolated and purified AML1-MTG8 fused mRNA comprising the contiguous nucleotide sequence consisting of SEQ ID No. 1 except that thymine is replaced with uracil.

4. An isolated and purified mRNA fragment of AML1-MTG8 fused mRNA comprising a fragment of the contiguous nucleotide sequence consisting of SEQ ID No. 1 except that thymine is replaced with uracil, which fragment contains nucleotides on the 5' and 3' side of the fused site of said AML1-MTG8 fused mRNA, said fused site being the site between bases 2110 and 2111, wherein said mRNA fragment specifically hybridizes with said nucleotide sequence of SEQ. ID. NO. 1 but does not specifically hybridize with AML1 DNA or MTG8 DNA.

5. A probe which is AML1-MTG8 fused DNA comprising the contiguous nucleotide sequence consisting of SEQ ID No. 1 or which is a DNA fragment comprising contiguous nucleotides on the 5' and 3' side of the fused site of AML1-MTG8 fused DNA, said fused site being the site between bases 2110 and 2111 of the nucleotide sequence consisting of SEQ ID No. 1, wherein said DNA fragment specifically hybridizes with the complement of said nucleotide sequence consisting of SEQ ID No. 1 but does not hybridize with AML1 DNA or MTG8 DNA that is labelled.

6. A method for detecting fused DNA containing the fused site of AML1-MTG8 fused DNA, said fused site being the site between bases 2110 and 2111 of the nucleotide sequence consisting of SEQ ID No. 1 which comprises:

contacting said probe of claim 5 with a sample to be tested; and determining whether said probe specifically hybridizes with said fused DNA in said sample but not with AML1 DNA or MTG8 DNA.

7. A probe which is a DNA or an RNA that is complementary to a fused AML1-MTG8 mRNA comprising the contiguous nucleotide sequence consisting of SEQ ID No. 1 except that thymine is replaced with uracil or to an mRNA fragment of AML1-MTG8 fused mRNA comprising a fragment of the contiguous nucleotide sequence consisting of SEQ ID No. 1 except that thymine is replaced with uracil, which fragment contains nucleotides on the 5' and 3' side of the fused site of said AML1-MTG8 fused mRNA, said fused site being the site between bases 2110 and 2111, wherein said mRNA fragment specifically hybridizes with said nucleotide sequence of SEQ. ID. NO. 1 but does not specifically hybridize with AML1 DNA or MTG8 DNA, said DNA or RNA being labelled.

8. A method for detecting AML1-MTG8 fused mRNA comprising the contiguous nucleotide sequence consisting of SEQ ID No. 1 except that thymine is replaced with uracil or an mRNA fragment of AML1-MTG8 fused mRNA comprising a fragment of the contiguous nucleotide sequence consisting of SEQ ID No. 1 except that thymine is replaced with uracil, which fragment contains nucleotides on the 5' and 3' side of the fused site of said AML1-MTG8 fused mRNA, said fused site being the site between bases 2110 and 2111, wherein said mRNA fragment specifically hybridizes with said nucleotide sequence of SEQ. ID. NO. 1 but does not specifically hybridize with AML1 DNA or MTG8 DNA which comprises:

contacting a labeled DNA or RNA probe that is complementary to said fused mRNA or to said mRNA fragment with a sample to be tested; and determining whether said probe has Specifically hybridized with said fused mRNA or said mRNA fragment in said sample but not with AML1 DNA or MTG8 DNA.

9. A method for detecting AML1-MTG8 fused DNA or a fragment thereof in a sample, comprising the steps of:

selectively amplifying AML1-MTG8 fused DNA comprising the contiguous nucleotide sequence consisting of SEQ ID No. 1 or a DNA fragment comprising contiguous nucleotides on the 5' and 3' side of the fused site of AML1-MTG8 fused DNA, said fused site being the site between bases 2110 and 2111 of the nucleotide sequence of SEQ ID No. 1, wherein said DNA fragment specifically hybridizes with said nucleotide sequence consisting of SEQ. ID. NO. 1 but does not specifically hybridize with AML1 DNA or MTG8 DNA by a nucleic acid-amplifying method; and detecting the amplified DNA fragment to determine whether said AML1-MTG8 fused DNA or said fragment thereof is present in said sample.

10. A method for detecting AML1-MTG8 fused mRNA or a fragment thereof in a sample, comprising the steps of:

selectively amplifying AML1-MTG8 fused mRNA comprising the contiguous nucleotide sequence consisting of SEQ ID No. 1 except that thymine is replaced with uracil or an mRNA fragment of AML1-MTG8 fused mRNA comprising a fragment of the contiguous nucleotide sequence consisting of SEQ ID No. 1 except that thymine is replaced with uracil, which fragment contains nucleotides on the 5' and 3' side of the fused site of said AML1-MTG8 fused mRNA, said fused site being the site between bases 2110 and 2111, wherein said mRNA fragment specifically hybridizes with said nucleotide sequence of SEQ. ID. NO. 1 but does not specifically hybridize with AML1 DNA or MTG8 DNA by a nucleic acid-amplifying method; and detecting the amplified RNA fragment to determine whether said AML1-MTG8 fused mRNA or said fragment thereof is present in said sample.

11. The fused DNA of claim 1 or the DNA fragment of claim 2, which specifically hybridizes to a DNA having a sequence set forth in SEQ. ID. NO. 1 under the following conditions (a) 6×SSC, 10% dextran sulfate, 1% SDS, 1×Denhart's solution, 50% formamide, 42° C. overnight or (b) 10 mM Tris-HCl pH 8.3, 50 mM potassium chloride, 3 mM magnesium chloride, 62° C., 30 seconds.

12. A pair of oligonucleotides wherein one of said oligonucleotides specifically hybridizes with AML1-MTG8 fused DNA comprising the contiguous nucleotide sequence consisting of SEQ ID No. 1 on the 3' side of a fused site which is the site between bases 2110 and 2111 of SEQ ID No. 1 and the other of said oligonucleotides specifically hybridizes with said AML1-MTG8 fused DNA on the 5' side of said fused site.

* * * * *